United States Patent
Young et al.

(10) Patent No.: US 7,456,259 B2
(45) Date of Patent: Nov. 25, 2008

(54) CANCEROUS DISEASE MODIFYING ANTIBODIES

(75) Inventors: David S. F. Young, Toronto (CA); Susan E. Hahn, Toronto (CA); Lisa M. Cechetto, Seoul (KR)

(73) Assignee: Arius Research, Inc., Toronto, Ontario (CA)

( * ) Notice: Subject to any disclaimer, the term of this patent is extended or adjusted under 35 U.S.C. 154(b) by 0 days.

(21) Appl. No.: 11/496,678

(22) Filed: Jul. 31, 2006

(65) Prior Publication Data

US 2007/0031429 A1    Feb. 8, 2007

Related U.S. Application Data

(60) Provisional application No. 60/704,685, filed on Aug. 2, 2005.

(51) Int. Cl.
| C07K 16/00 | (2006.01) |
| C12P 21/08 | (2006.01) |
| A61K 39/00 | (2006.01) |
| G01N 33/53 | (2006.01) |
| A61K 39/395 | (2006.01) |

(52) U.S. Cl. ............ 530/387.1; 530/387.3; 530/388.1; 530/388.8; 530/391.1; 424/133.1; 424/141.1; 424/155.1; 424/174.1; 435/7.1

(58) Field of Classification Search ............ None
See application file for complete search history.

(56) References Cited

U.S. PATENT DOCUMENTS

| 4,433,059 A * | 2/1984 | Chang et al. ............ 436/512 |
| 4,816,567 A | 3/1989 | Cabilly et al. |
| 4,861,581 A | 8/1989 | Epstein et al. |
| 5,171,665 A | 12/1992 | Hellstrom et al. |
| 5,484,596 A | 1/1996 | Hanna, Jr. et al. |
| 5,500,362 A | 3/1996 | Robinson et al. |
| 5,591,828 A | 1/1997 | Bosslet et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,821,337 A | 10/1998 | Carter et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 7,189,825 B2 * | 3/2007 | Young et al. ............ 530/388.1 |
| 2005/0191305 A1 * | 9/2005 | Young et al. ............ 424/155.1 |

FOREIGN PATENT DOCUMENTS

| CA | 2456077 | 12/2003 |
| CA | 2557091 | 9/2005 |
| CA | 2557093 | 9/2005 |
| EP | 0266032 | 5/1988 |
| WO | WO9311161 | 6/1993 |
| WO | WO0034317 | 6/2000 |
| WO | WO2004065420 | 8/2004 |
| WO | WO2004065421 | 8/2004 |
| WO | WO2005012361 | 2/2005 |

OTHER PUBLICATIONS

L. Belanger et al, "Enzyme-linked imunnoassay for alpha-fetoprotein by competitive and sandwich procedures", Clinica Chimica Acta, 48:15-18 (1973).
M. Bendandi et al, "Complete molecular remissions induced by patient-specific vaccination plus granulocyte-monocyte colony-stimulating factor against lymphoma", Nature Medicine, 5(10):1171-1177 (Oct. 1999).
P. Capel et al, "Heterogeneity of human IgG Fc receptors", Immunomethods, 4:25-34 (1994).
C. Chothia et al, "Canonical structures for the hypervariable regions of immunoglobulins", J. Mol. Biol., 196:901-917 (1987).
T. Clackson et al, "Making antibody fragments using phage display libraries", Nature, 352-624-628 (Aug. 1991).
R. Clynes et al, "Fc receptors are required in passive and active immunity to melanoma", Proc. Natl. Acad. Sci. USA, 95:652-656 (Jan. 1998).
S. Eckhardt et al, "Developmental therapeutics: successes and failures of clinical trial designs of targeted compounds", ASCO Educational Book, 39th Annual Meeting, pp. 209 (2003).
B. Froehler et al, "Synthesis of DNA via deoxynucleoside H-phosphonate intermediates", Nucleic Acids Research, 14(13):5399-5407 (1986).

(Continued)

*Primary Examiner*—David J. Blanchard
*Assistant Examiner*—Anne M. Gussow
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

20 Claims, 7 Drawing Sheets

OTHER PUBLICATIONS

H. Gazzano-Santoro et al, "A non-radioactive complement-dependent cytotoxicity assay for anti-CD20 monoclonal antibody", J. Immunol. Methods, 202:163-171 (1997).

R. Guyer et al, "Immunoglobin binding by mouse intestinal epithelial cell receptors", J. Immunol., 117(2):587-593 (Aug. 1976).

M. De Haas et al, "Review articles: FCγ receptors of phagocytes", J. Lab Clin. Med., 126:330-341 (1995).

S. Hirschfeld et al, "Oncology drug development: United States Food and Drug Administration Perspective", Critical Reviews in Oncology/Hematology, 42:137-143 (2002).

P. Holliger et al, "Diabodies: small bivalent and bispecific antibody fragments", Proc. Natl. Acad. Sci. USA, 90:6444-6448 (Jul. 1993).

E. Kabat et al, "Sequences of proteins of immunological interest", 5th ed. Public Health Service, National Institutes of Health, Bethesda, MD (1991).

J. Kim et al, "Localization of the site of the murine IgG1 molecule that is involved in binding to the murine intestinal Fc receptor", Eur. J. Immunol., 24:2429-2434 (1994).

G. Kohler et al, "Continuous cultures of fused cells secreting antibody of predefined specificity", Nature, 256:495-497 (Aug. 1975).

J. Marks et al, "By-passing immunization human antibodies from V-gene libraries displayed on phage", J. Mol. Biol., 222:581-597 (1991).

M. Daeron, "Fc receptor biology", Annu. Rev. Immunol., 15:203-234 (1997).

S. Morrison et al, "Chimeric human antibody molecules: mouse antigen binding domains with human constant region domains", Proc. Natl. Acad. Sci. USA, 81:6851-6855 (Nov. 1984).

A. Pluckthun, "Antibodies from *Escherichia coli*", Handbook of Experimental Pharmacology, vol. 113, Chapter 11, pp. 269-315, Springer-Verlag, New York (1994).

M. Schuster et al, "Cancer immunotherapy", Biotechnology Journal, 1:138-147 (2006).

P. Therasse et al, "New guidelines to evaluate the response to treatment in solid tumors", J. Natl. Cancer Inst., 92:205-216 (2000).

J. Rubinstein et al, "Use of phage display and high-density screening for the isolation of an antibody against the 51-kDa subunit of complex I", Analytical Biochemistry, 314:294-300 (2003).

J. Ravetch et al, "Fc receptors", Annu. Rev. Immunol., 9:457-492 (1991).

\* cited by examiner

FIGURE 1

| | Isotype ELISA Fold | | Percentage Cytotoxicity | | | | | | | | | | Binding | | | | |
|---|---|---|---|---|---|---|---|---|---|---|---|---|---|---|---|---|---|
| | | | MDA-MB-231 | | OVCAR-3 | | SW1116 | | Lovo | | CCD-27sk | | MDA-MB-231 | OVCAR-3 | SW1116 | Lovo | CCD-27sk |
| | IgG | IgM | Average | CV | Average | CV | Average | CV | Average | CV | Average | CV | Fold | Fold | Fold | Fold | Fold |
| AR62A61.8 | 9.2 | 0.8 | 1 | 9 | 22 | 6 | -3 | 4 | 15 | 9 | -5 | 3 | 4.8 | 2.5 | 1.5 | 2.2 | 1.3 |
| Controls Cyclohexamide | | | 56 | 6 | 36 | 27 | 24 | 37 | 87 | 3 | 29 | 17 | | | | | |
| NaN₃ | | | 51 | 6 | 60 | 13 | | | 48 | 20 | 4 | 151 | | | | | |
| c225 | | | | | | | 41 | 10 | | | | | | | | | |

FIGURE 2

| | Cell Line | Colon | | | Breast | Ovary | Normals | |
|---|---|---|---|---|---|---|---|---|
| | | DLD-1 | Lovo | SW1116 | MDA-MB-231 | OVCAR-3 | CCD-27sk | Hs888.Lu |
| | AR62A61.8 | 4.8 | 0.9 | 1.8 | 3.8 | 2.4 | 1.2 | 3.8 |
| Positive Controls | anti-EGFR | 7.2 | 2.0 | 1.9 | 3.7 | 1.6 | 1.4 | 3.2 |

CANCEROUS DISEASE MODIFYING ANTIBODIES

REFERENCE TO RELATED APPLICATIONS

This application claims benefit of the filing date of Provisional Application 60/704,685, filed on Aug. 2, 2005, the contents of which are herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMAB of the instant invention.

BACKGROUND OF THE INVENTION

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remissions or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her 2/neu antibody (HERCEPTIN®) in combination with cisplatin. In this trial 37 patients were assessed for responses of which about a quarter had a partial response rate and an additional quarter had minor or stable disease progression. The median time to progression among the responders was 8.4 months with median response duration of 5.3 months.

HERCEPTIN® was approved in 1998 for first line use in combination with TAXOL®. Clinical study results showed an increase in the median time to disease progression for those who received antibody therapy plus TAXOL® (6.9 months) in comparison to the group that received TAXOL® alone (3.0 months). There was also a slight increase in median survival; 22 versus 18 months for the HERCEPTIN® plus TAXOL® treatment arm versus the TAXOL® treatment alone arm. In addition, there was an increase in the number of both complete (8 versus 2 percent) and partial responders (34 versus 15 percent) in the antibody plus TAXOL® combination group in comparison to TAXOL® alone. However, treatment with HERCEPTIN® and TAXOL® led to a higher incidence of cardiotoxicity in comparison to TAXOL® treatment alone (13 versus 1 percent respectively). Also, HERCEPTIN® therapy was only effective for patients who over express (as determined through immunohistochemistry (IHC) analysis) the human epidermal growth factor receptor 2 (Her2/neu), a receptor, which currently has no known function or biologically important ligand. Only about 25 percent of patients who have metastatic breast cancer overexpress Her2/neu therefore, there is still a large unmet need for patients with breast cancer. Even those who can benefit from HERCEPTIN® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like HERCEPTIN®, treatment in Switzerland is only approved as a combination of monoclonal antibody and chemotherapy. In addition, treatment in both Switzerland and the U.S. is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like HERCEPTIN® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXOTERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including HERCEPTIN® and RITUXIMAB®, have been produced using these methods and selected on the basis of their affinity. The flaws in this strategy are two-fold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, has been inadequate for all types of cancer.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single-chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

This application utilizes methodology for producing patient specific anti-cancer antibodies taught in the U.S. Pat. No. 6,180,357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinities of these antibodies are suited to requirements for initiation of the cytotoxic events that may not be amenable to stronger affinity interactions. Also, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy, survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39$^{th}$ Annual Meeting, 2003, pages 209-219).

The present invention describes the development and use of AR62A61.8 identified by its effect in a cytotoxic assay and in an animal model of human cancer. This invention describes reagents that bind specifically to an epitope or epitopes present on the target molecule, and that also have in vitro cytotoxic properties, as a naked antibody, against malignant tumor cells but not normal cells, and which also directly mediate, as a naked antibody, inhibition of tumor growth. A further advance is of the use of anti-cancer antibodies such as this to target tumors expressing cognate antigen markers to achieve tumor growth inhibition, and other positive endpoints of cancer treatment.

In all, this invention teaches the use of the AR62A61.8 antigen as a target for a therapeutic agent, that when administered can reduce the tumor burden of a cancer expressing the antigen in a mammal. This invention also teaches the use of CDMAB (AR62A61.8), and their derivatives, and antigen binding fragments thereof, and cellular cytotoxicity inducing ligands thereof, to target their antigen to reduce the tumor burden of a cancer expressing the antigen in a mammal. Furthermore, this invention also teaches the use of detecting the AR62A61.8 antigen in cancerous cells that can be useful for the diagnosis, prediction of therapy, and prognosis of mammals bearing tumors that express this antigen.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

FIG. 1 compares the percentage cytotoxicity and binding levels of the hybridoma supernatants against cell lines MDA-MB-231, OVCAR-3, SW1116, Lovo, and CCD-27sk.

FIG. 2 represents binding of AR62A61.8 and the anti-EGFR control to cancer and normal cell lines. The data is tabulated to present the mean fluorescence intensity as a fold increase above isotype control.

DETAILED DESCRIPTION OF THE INVENTION

Figure 3:
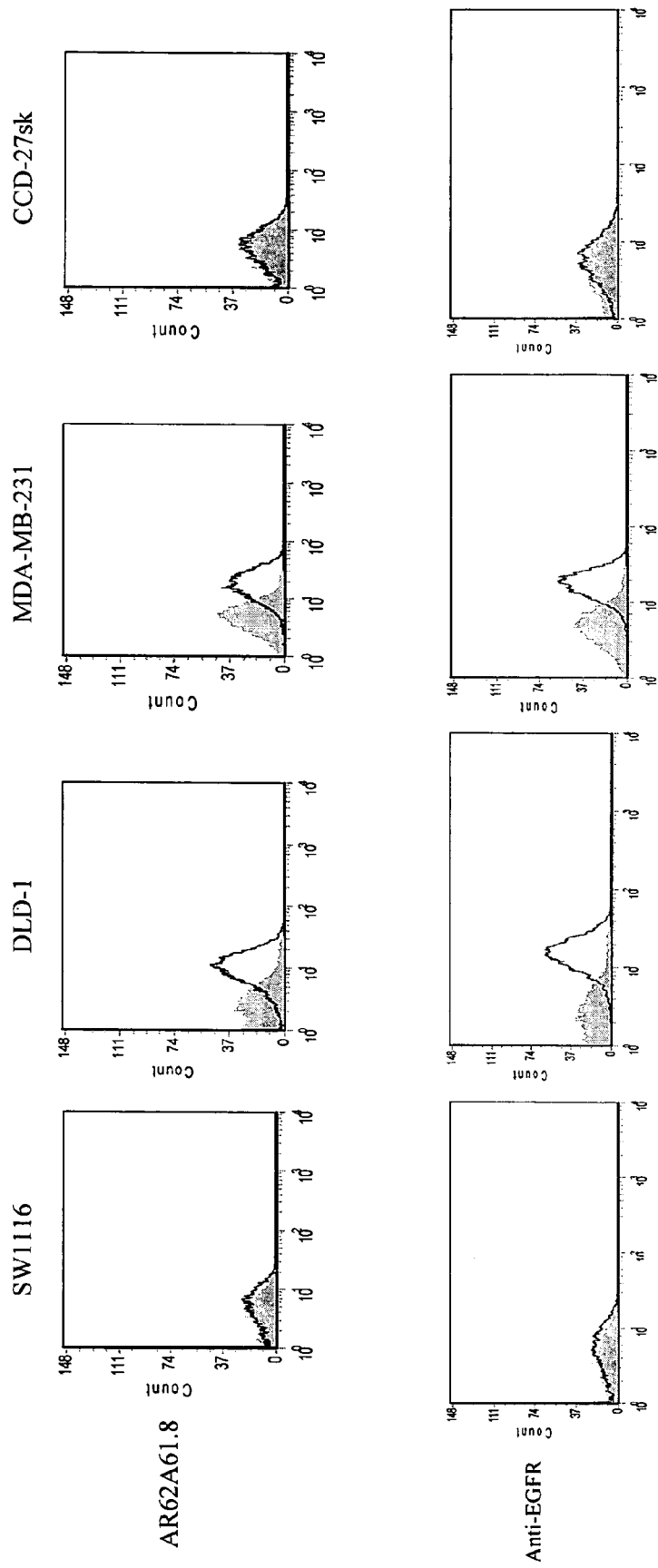
FIG. 3 includes representative FACS histograms of AR62A61.8 and anti-EGFR antibodies directed against several cancer and non-cancer cell lines.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimerized or humanized antibodies), antibody compositions with polyepitopic specificity, single-chain antibodies, immunoconjugates and fragments of antibodies (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or an amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, Annu. Rev. Immunol. 15:203-234 (1997)). FcRs are reviewed in avetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., Eur. J. Immunol. 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996) may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. pp 15-17; 48-53 (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of proteins of Immunological Interest,* 5th Ed. Public Health Service, National Institutes of Health, Bethesda, Md. pp 15-17; 48-53 (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies,* vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful as a therapeutic or diagnostic agent in targeting a cell expressing the antigen. Where the antibody is one which binds the antigenic moiety it will usually preferentially bind that antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as antiestrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399-5407, 1986. They are then purified on polyacrylamide gels.

"Chimeric" antibodies are immunoglobulins in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al, *Proc. Natl. Acad. Sci. USA,* 81:6851-6855 (1984)).

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

An antibody which induces "apoptosis" is one which induces programmed cell death by any means, illustrated by but not limited to binding of annexin V, caspase activity, fragmentation of DNA, cell shrinkage, dilation of endoplasmic reticulum, cell fragmentation, and/or formation of membrane vesicles (called apoptotic bodies).

Throughout the instant specification, hybridoma cell lines, as well as the isolated monoclonal antibodies which are produced therefrom, are alternatively referred to by their internal designation, AR62A61.8 or Depository Designation, IDAC 170505-04.

As used herein "antibody-ligand" includes a moiety which exhibits binding specificity for at least one epitope of the target antigen, and which may be an intact antibody molecule, antibody fragments, and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds at least one epitope of the antigen bound by the isolated monoclonal antibody produced by the hybridoma cell line designated as IDAC 170505-04 (the IDAC 170505-04 antigen).

As used herein "cancerous disease modifying antibodies" (CDMAB) refers to monoclonal antibodies which modify the cancerous disease process in a manner which is beneficial to the patient, for example by reducing tumor burden or prolonging survival of tumor bearing individuals, and antibody-ligands thereof.

As used herein "antigen-binding region" means a portion of the molecule which recognizes the target antigen.

As used herein "competitively inhibits" means being able to recognize and bind a determinant site to which the monoclonal antibody produced by the hybridoma cell line designated as IDAC 170505-04, (the IDAC 170505-04 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the IDAC 170505-04 antigen or portions thereof.

As used herein, an "immunoconjugate" means any molecule or CDMAB such as an antibody chemically or biologically linked to a cytotoxin, a radioactive agent, enzyme, toxin, an anti-tumor drug or a therapeutic agent. The antibody or CDMAB may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, a "fusion protein" means any chimeric protein wherein a antigen binding region is connected to a biologically active molecule, e.g., toxin, enzyme, or protein drug.

In order that the invention herein described may be more fully understood, the following description is set forth.

The present invention provides CDMABs (i.e., IDAC 170505-04 CDMAB) which specifically recognize and bind the IDAC 170505-04 antigen.

The CDMAB of the isolated monoclonal antibody produced by the hybridoma deposited with the IDAC as accession number 170505-04 may be in any form as long as it has an antigen-binding region which competitively inhibits the immunospecific binding of the isolated monoclonal antibody produced by hybridoma IDAC 170505-04 to its target antigen. Thus, any recombinant proteins (e.g., fusion proteins wherein the antibody is combined with a second protein such as a lymphokine or a tumor inhibitory growth factor) having the same binding specificity as the IDAC 170505-04 antibody fall within the scope of this invention.

In one embodiment of the invention, the CDMAB is the IDAC 170505-04 antibody.

In other embodiments, the CDMAB is an antigen binding fragment which may be a Fv molecule (such as a single-chain Fv molecule), a Fab molecule, a Fab' molecule, a F(ab')2 molecule, a fusion protein, a bispecific antibody, a heteroantibody or any recombinant molecule having the antigen-binding region of the IDAC 170505-04 antibody. The CDMAB of the invention is directed to the epitope to which the IDAC 170505-04 monoclonal antibody is directed.

The CDMAB of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the IDAC 170505-04 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Given an antibody, an individual ordinarily skilled in the art can generate a competitively inhibiting CDMAB, for example a competing antibody, which is one that recognizes the same epitope (Belanger L et al. *Clinica Chimica Acta* 48:15-18 (1973)). One method entails immunizing with an immunogen that expresses the antigen recognized by the antibody. The sample may include but is not limited to tissues, isolated protein(s) or cell line(s). Resulting hybridomas could be screened using a competition assay, which is one that identifies antibodies that inhibit the binding of the test antibody, such as ELISA, FACS or Western blotting. Another method could make use of phage display antibody libraries and panning for antibodies that recognize at least one epitope of said antigen (Rubinstein J L et al. *Anal Biochem* 314:294-300 (2003)). In either case, antibodies are selected based on their ability to out-compete the binding of the original labeled antibody to at least one epitope of its target antigen. Such antibodies would therefore possess the characteristic of recognizing at least one epitope of the antigen as the original antibody.

EXAMPLE 1

Hybridoma Production—Hybridoma Cell Line AR62A61.8

The hybridoma cell line AR62A61.8 was deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on May 17, 2005, under Accession Number 170505-04. In accordance with 37 CFR 1.808, the depositors assure that all restrictions imposed on the availability to the public of the deposited materials will be irrevocably removed upon the granting of a patent. The deposit will be replaced if the depository cannot dispense viable samples.

To produce the hybridoma that produces the anti-cancer antibody AR62A61.8, a single cell suspension of frozen human prostate tumor tissue (Genomics Collaborative, Cambridge, Mass.) was prepared in PBS. IMMUNEASY™ (Qiagen, Venlo, Netherlands) adjuvant was prepared for use by gentle mixing. Five to seven week old BALB/c mice were immunized by injecting subcutaneously, 2 million cells in 50 microliters of the antigen-adjuvant. Recently prepared antigen-adjuvant was used to boost the immunized mice intraperitoneally, 2 and 5 weeks after the initial immunization, with 2 million cells in 50 microliters. A spleen was used for fusion three days after the last immunization. The hybridomas were prepared by fusing the isolated splenocytes with NSO-1 myeloma partners. The supernatants from the fusions were tested from subclones of the hybridomas.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1 M carbonate/bicarbonate buffer, pH 9.2-9.6) at 4° C. was added to the ELISA plates overnight. The plates were washed thrice in washing buffer (PBS+0.05 percent Tween). 100 microliters/well blocking buffer (5 percent milk in wash buffer) was added to the plate for 1 hour at room temperature and then washed thrice in washing buffer. 100 microliters/well of hybridoma supernatant was added and the plate incubated for 1 hour at room temperature. The plates were washed thrice with washing buffer and 1/100,000 dilution of either goat anti-mouse IgG or IgM horseradish peroxidase conjugate (diluted in PBS containing 5 percent milk), 100 microliters/well, was added. After incubating the plate for 1 hour at room temperature the plate was washed thrice with washing buffer. 100 microliters/well of TMB solution was incubated for 1-3 minutes at room temperature. The color reaction was terminated by adding 50 microliters/well 2M $H_2SO_4$ and the plate was read at 450 nm with a Perkin-Elmer HTS7000 plate reader. As indicated in FIG. 1, the AR62A61.8 hybridoma secreted primarily antibodies of the IgG isotype.

To determine the subclass of antibody secreted by the hybridoma cells, an isotyping experiment was performed using a Mouse Monoclonal Antibody Isotyping Kit (HyCult Biotechnology, Frontstraat, Netherlands). 500 microliters of buffer solution was added to the test strip containing rat anti-mouse subclass specific antibodies. 500 microliters of hybridoma supernatant was added to the test tube, and submerged by gentle agitation. Captured mouse immunoglobulins were detected directly by a second rat monoclonal antibody which is coupled to colloid particles. The combination of these two proteins creates a visual signal used to analyse the isotype. The anti-cancer antibody AR62A61.8 is of the IgG1, κ isotype.

After one round of limiting dilution, hybridoma supernatants were tested for antibodies that bound to target cells in a cell ELISA assay. One human breast cancer cell line, 1 human ovarian cancer cell line, 2 human colon cancer cell lines, and 1 human normal skin cell line were tested: MDA-MB-231, OVCAR-3, SW1116, Lovo, and CCD-27sk respectively. All cell lines were obtained from the American Type Tissue Collection (ATCC; Manassas, Va.). The plated cells were fixed prior to use. The plates were washed thrice with PBS containing $MgCl_2$ and $CaCl_2$ at room temperature. 100 microliters of 2 percent paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5 percent milk in wash buffer (PBS+0.05 percent Tween) for 1 hour at room temperature. The plates were washed thrice with wash buffer and the hybridoma supernatant was added at 75 microliters/well for 1 hour at room temperature. The plates were washed 3 times with wash buffer and 100 microliters/well of 1/25, dilution of goat anti-mouse IgG or IgM antibody conjugated to horseradish peroxidase (diluted in PBS containing 5 percent milk) was added. After 1 hour incubation at room temperature the plates were washed 3 times with wash buffer and 100 microliter/well of TMB substrate was incubated for 1-3 minutes at room temperature. The reaction was terminated with 50 microliters/well 2M $H_2SO_4$ and the plate read at 450 nm with a Perkin-Elmer HTS7000 plate reader. The results as tabulated in FIG. 1 were expressed as the number of folds above background compared to an in-house IgG isotype control that has previously been shown not to bind to the cell lines tested. The antibodies from the hybridoma AR62A61.8 showed substantial binding to the breast cancer cell line MDA-MB-231, followed by the ovarian cancer cell line OVCAR-3, and the colon cancer cell lines Lovo and SW1116. AR62A61.8 displayed a low level of binding to the normal skin cell line CCD-27sk.

In conjunction with testing for antibody binding, the cytotoxic effect of the hybridoma supernatants was tested in the cell lines: MDA-MB-231, OVCAR-3, SW1116, Lovo and CCD-27sk. Calcein AM was obtained from Molecular Probes (Eugene, Oreg.) and the assay was performed as outlined below. Cells were plated before the assay at the predetermined appropriate density. After 2 days, 75 microliters of supernatant from the hybridoma microtitre plates were transferred to the cell plates and incubated in a 5 percent $CO_2$ incubator for 5 days. The wells that served as the positive controls were aspirated until empty and 100 microliters of sodium azide sodium azide ($NaN_3$, 0.01 percent, Sigma, Oakville, ON), cycloheximide (CHX, 0.5 micromolar, Sigma, Oakville, ON) or anti-EGFR antibody (c225, IgG1, kappa, 5 micrograms/mL, Cedarlane, Homby, ON) was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel. The results are tabulated in FIG. 1. Supernatant from the AR62A61.8 hybridoma produced specific cytotoxicity of 22 percent on the OVCAR-3 cells and 15 percent on the Lovo cells. This was 37 and 61 percent of the cytotoxicity obtained with the positive controls sodium azide and cycloheximide respectively for OVCAR-3, and likewise, 31 and 17 percent for the Lovo cells. There was no observable cytotoxicity to the normal skin cell line CCD-27sk. The known non-specific cytotoxic agents cycloheximide and $NaN_3$ generally produced cytotoxicity as expected. The anti-EGFR antibody c225 produced cytotoxicity as expected on SW1116.

Results from FIG. 1 demonstrated that the cytotoxic effects of AR62A61.8 on the different cell lines did not necessarily correlate to the level of binding. Although the breast cancer cell line MDA-MB-231 exhibited the highest degree of binding, there was no cytotoxicity directed at this cell line. There was a greater level of cytotoxicity produced in the OVCAR-3 cells as compared to the Lovo cells, which corresponded to a slightly higher level of binding in the OVCAR-3 ovarian cancer cell line. The antibody therefore exhibited functional specificity, which was not necessarily related to the degree of binding.

EXAMPLE 2

In Vitro Binding

AR62A61.8 monoclonal antibody was produced by culturing the hybridoma in CL-1000 flasks (BD Biosciences, Oakville, ON) with collections and reseeding occurring twice/week. Standard antibody purification procedures with Protein G Sepharose 4 Fast Flow (Amersham Biosciences, Baie d'Urfé, QC) were followed. It is within the scope of this invention to utilize monoclonal antibodies that are humanized, de-immunized, chimerized or murine.

Binding of AR62A61.8 to breast (MDA-MB-231), colon (DLD-1, Lovo, SW1116) and ovarian (OVCAR-3) cancer, and non-cancer cell lines from skin (CCD-27sk) and lung (Hs888.Lu) was assessed by flow cytometry (FACS). All cell lines were obtained from the American Type Tissue Collection (ATCC; Manassas, Va.). Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection, the cells were resuspended in DPBS containing $MgCl_2$, $CaCl_2$ and 2 percent fetal bovine serum at 4° C. (staining media) and counted, aliquoted to appropriate cell density, spun down to pellet the cells and resuspended in staining media at 4° C. in the presence of test antibodies (AR62A61.8) or control antibodies (isotype control, anti-EGFR) at 20 micrograms/mL on ice for 30 minutes. Prior to the addition of Alexa Fluor 546-conjugated secondary antibody the cells were washed once with staining media. The Alexa Fluor 546-conjugated antibody in staining media was then added for 30 minutes at 4° C. The cells were then washed for the final time and resuspended in fixing media (staining media containing 1.5 percent paraformaldehyde). Flow cytometric acquisition of the cells was assessed by running samples on a FACSarray™ using the FACSarray™ System Software (BD Biosciences, Oakville, ON). The forward (FSC) and side scatter (SSC) of the cells were set by adjusting the voltage and amplitude gains on the FSC and SSC detectors. The detectors for the fluorescence (Alexa-546) channel was adjusted by running unstained cells such that cells had a uniform peak with a median fluorescent intensity of approximately 1-5 units. For each sample, approximately 10,000 gated events (stained fixed cells) were acquired for analysis and the results are presented in FIG. 2.

FIG. 2 presents the mean fluorescence intensity fold increase above isotype control. Representative histograms of AR62A61.8 antibodies were compiled for FIG. 3. AR62A61.8 showed strongest binding to the colon cancer cell lines DLD-1 (4.8-fold), the normal lung cell line Hs888.Lu (3.8-fold) and the breast cancer cell line MDA-MB-231 (3.8-fold), with lower levels of binding seen in the colon cancer cell line SW1116 (1.8-fold) and the ovarian cancer cell line OVCAR-3 (2.4-fold). Under these conditions, no binding was observed to the Lovo colon cancer cell line or to the normal skin cell line CCD-27sk. These data demonstrate that AR62A61.8 binds selectively to different human cell lines.

EXAMPLE 3

In Vivo Tumor Experiments with Lovo Cells

Figure 4:
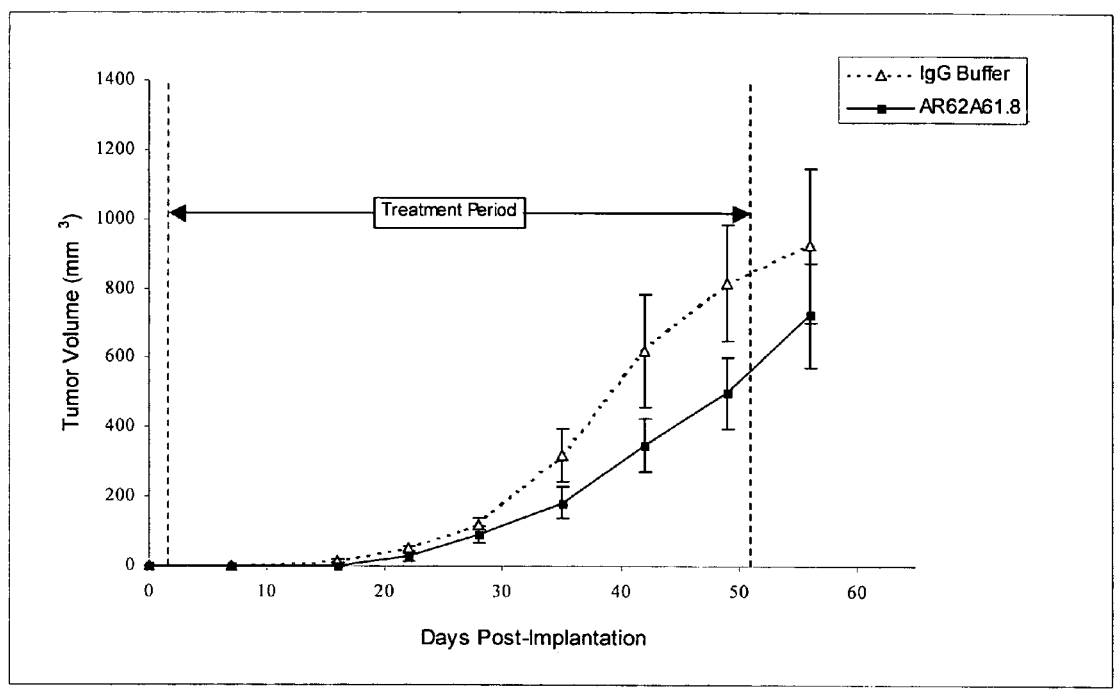
FIG. 4 demonstrates the effect of AR62A61.8 on tumor growth in a prophylactic Lovo colon cancer model. The vertical lines indicate the period during which the antibody was administered. Data points represent the mean +/− SEM.
Figure 5:
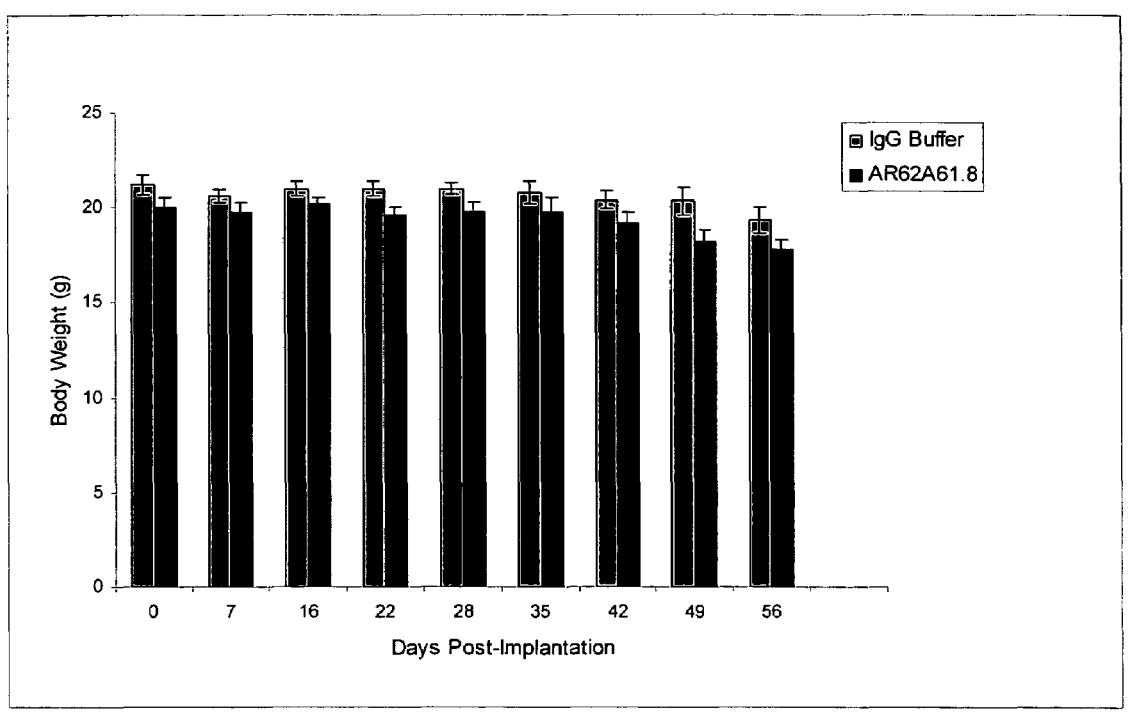
FIG. 5 demonstrates the effect of AR62A61.8 on body weight in a prophylactic Lovo colon cancer model. Data points represent the mean +/− SEM.
Figure 6:
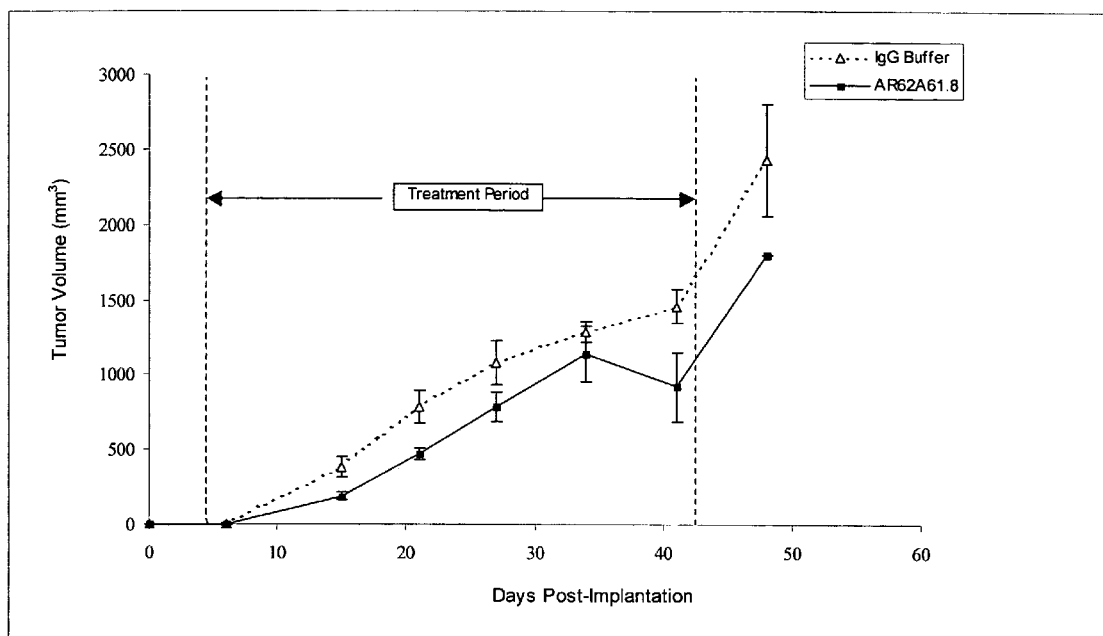
FIG. 6 demonstrates the effect of AR62A61.8 on tumor growth in a prophylactic DLD-1 colon cancer model. The vertical lines indicate the period during which the antibody was administered. Data points represent the mean +/− SEM.
Figure 7:
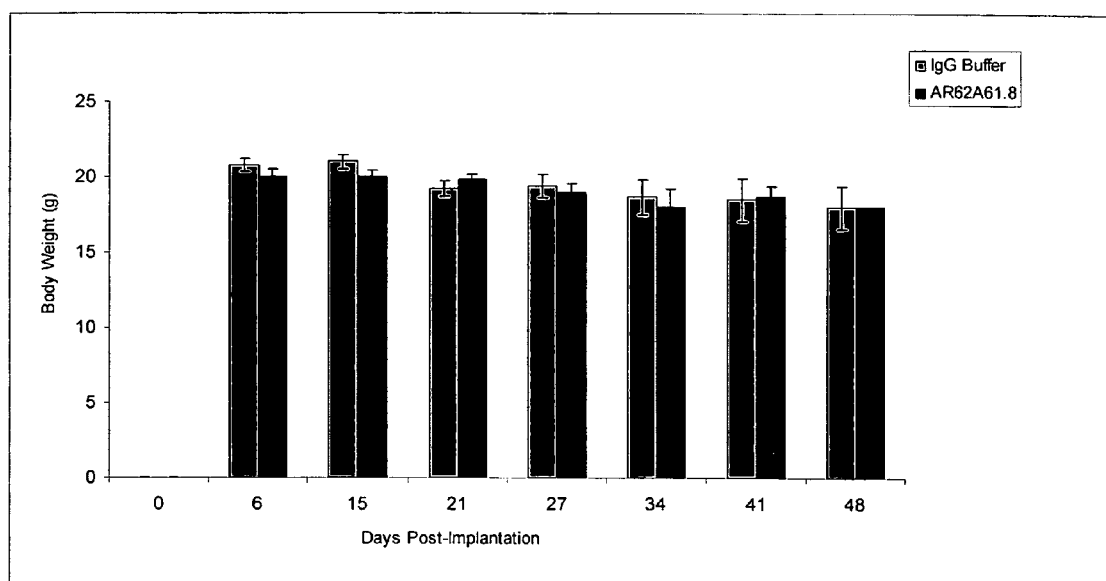
FIG. 7 demonstrates the effect of AR62A61.8 on body weight in a prophylactic DLD-1 colon cancer model. Data points represent the mean +/− SEM.

Examples 1 and 2 demonstrated that AR62A61.8 had anticancer properties against colon and ovarian cancer cell lines and demonstrated binding to colon cell types. With reference to FIGS. 4 and 5, 4 to 6 week old female SCID mice were implanted with 1 million human colon cancer cells (Lovo) in 100 microlitres saline injected subcutaneously in the scruff of the neck. The mice were randomly divided into 2 treatment groups of 5. On the day after implantation, 20 mg/kg of AR62A61.8 test antibody or buffer control was administered intraperitoneally to each cohort in a volume of 300 microlitres after dilution from the stock concentration with a diluent that contained 2.7 mM KCl, 1 mM $KH_2PO_4$, 137 mM NaCl and 20 mM $Na_2HPO_4$. The antibody and control samples were then administered once per week for a period of 7 weeks in the same fashion. Tumor growth was measured about every seventh day with calipers for up to 8 weeks or until individual animals reached Canadian Council for Animal Care (CCAC) endpoints. Body weights of the animals were recorded once per week for the duration of the study. At the end of the study all animals were euthanized according to CCAC guidelines.

AR62A61.8 reduced the tumor burden in an in vivo prophylactic model of human colon cancer. On day 56 post-implantation, 6 days after the last treatment dose, the mean tumor volume in the AR62A61.8 treated group was 22 percent less than that of the buffer control-treated group (FIG. 4). Average tumor volumes at the final timepoint were influenced by the loss of mice due to ulcerated lesions before the termination of the treatment period. At Day 42, when all mice were still alive, AR62A61.8 caused a 44 percent decrease in tumor volume compared to buffer-treated control mice (p=0.171).

There were no clinical signs of toxicity throughout the study. Body weight, shown in FIG. 5, was used as a surrogate for well-being and failure to thrive. Within groups, there was a nonsignificant 9 percent decrease in body weight in the control group over the duration of the study, while the body weight of the AR62A61.8 treated group showed an 11 percent decrease from a mean of 20 g to 17.8 g. There was no significant difference in body weight between the groups at the end of the treatment period (p=0.13, t-test). In summary, AR62A61.8 was well-tolerated and decreased the tumor burden in this human colon cancer xenograft model. From Example 2, it is evident that the binding of AR62A61.8 to the Lovo cell line is not detectable using FACS. Nevertheless, the antibody was able to reduce the tumor growth in a Lovo xenograft model. The efficacy may be due to either of 2 factors. It is possible that the Lovo cell line expresses the antigen target at a level below the threshold of detection by FACS under these conditions, but that the low level of expression is sufficient to trigger an event leading to delayed tumor growth. It is also possible that antigen expression is induced when the Lovo cells are placed into the more physiological in vivo environment. In either case, the efficacy of this antibody in a Lovo colon cancer model is a non-obvious finding that could not have been predicted on the basis of binding.

EXAMPLE 4

In Vivo Tumor Experiments with DLD-1 Cells

Results from Example 3 were extended to a different model of human colon cancer. With reference to FIGS. 6 and 7, 4 to 6 week old female SCID mice were implanted with 5 million human colon cancer cells (DLD-1) in 100 microlitres saline injected subcutaneously in the scruff of the neck. The mice were randomly divided into 2 treatment groups of 5. On the day after implantation, 20 mg/kg of AR62A61.8 test antibody or buffer control was administered intraperitoneally to each cohort in a volume of 300 microlitres after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study in the same fashion. Tumor growth was measured about every seventh day with calipers. The study was completed after 7 injections (48 days), as the animals reached CCAC end-points due to large ulcerated lesions. Body weights of the animals were recorded once per week for the duration of the study. At the end of the study all animals were euthanized according to CCAC guidelines.

AR62A61.8 reduced tumor growth in the highly aggressive DLD-1 in vivo prophylactic model of human colon cancer. On day 41 days post-implantation, at around the time of the last treatment dose, the mean tumor volume in the AR62A61.8 treated group was 37 percent lower than the tumor volume in the buffer control-treated group (FIG. 6). Although the tumor burden of AR62A61.8-treated mice was lower than that of control-treated mice, the difference was non-significant in this aggressive model of human colon cancer. Average tumor volumes at the final timepoint were influenced by the loss of mice due to ulcerated lesions before the termination of the treatment period. At Day 27, when all mice were still alive, AR62A61.8 caused a 28 percent decrease in tumor volume (p=0.13). This decrease was observed after only 4 injections of the antibody. These in vivo results, in conjunction with the results presented in Example 2, demonstrate that AR62A61.8 is able to bind strongly to the DLD-1 cell line, as well as induce cytotoxicity in another colon model.

There were no clinical signs of toxicity throughout the study. Body weight measured at weekly intervals was a surrogate for well-being and failure to thrive. As seen in FIG. 8, there were no significant differences in the body weights of the control or 62A335.9-treated groups over the course of the study. There was also no difference in body weight between the two groups at the end of the treatment period (p=0.921, t-test).

Therefore AR62A61.8 was well-tolerated and decreased the tumor burden in this human colon cancer xenograft model.

The preponderance of evidence shows that AR62A61.8 mediates anti-cancer effects through ligation of an epitope present on cancer cell lines. Further it could be shown that the AR62A61.8 antibody could be used in detection of cells and/or tissues which express the epitope which specifically binds thereto, utilizing techniques illustrated by, but not limited to FACS, cell ELISA or IHC.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. The isolated monoclonal antibody produced by the hybridoma deposited with the IDAC as accession number 170505-04.

2. A humanized version of the isolated monoclonal antibody of claim 1.

3. A chimeric version of the isolated monoclonal antibody of claim 1.

4. The isolated hybridoma cell line deposited with the IDAC as accession number 170505-04.

5. A method for initiating antibody induced cellular cytotoxicity of cancerous cells in a tissue sample selected from a human tumor comprising:
   providing a tissue sample from said human tumor; providing the isolated monoclonal antibody produced by the hybridoma deposited with the IDAC as accession number 170505-04, a humanized version thereof, a chimeric version thereof, or an antigen binding fragment thereof; and
   contacting said isolated monoclonal antibody, said humanized version thereof, said chimeric version thereof or said antigen binding fragment thereof with said tissue sample;
   wherein binding of said isolated monoclonal antibody, said humanized version thereof, said chimeric version thereof or said antigen binding fragment thereof with said tissue sample induces cellular cytotoxicity.

6. Antigen binding fragments of the isolated monoclonal antibody of claim 1.

7. Antigen binding fragments of the humanized antibody of claim 2.

8. Antigen binding fragments of the chimeric antibody of claim 3.

9. The isolated antibody or antigen binding fragment, of any one of claims 1, 2, 3, 6, 7 or 8 conjugated with a member selected from the group consisting of cytotoxic moieties, enzymes, radioactive compounds, and hematogenous cells.

10. A binding assay to determine a presence of cancerous cells in a tissue sample selected from a human tumor, which is specifically bound by the isolated monoclonal antibody produced by hybridoma cell line AR62A61.8 having IDAC Accession No. 170505-04, comprising:
   providing a tissue sample from said human tumor;
   providing the recognized by the isolated monoclonal antibody produced by a hybridoma cell line AR62A61.8 having IDAC Accession No. 170505-04, a humanized version thereof, a chimeric version thereof, or an antigen binding fragment thereof, or at least one isolated monoclonal antibody or antigen binding fragment thereof that specifically binds to the same epitope or epitopes as those recognized by the Isolated monoclonal antibody produced by a hybridoma cell line AR62A61.8 having IDAC Accession No. 170505-04;
   contacting said monoclonal antibody, a humanized version thereof, a chimeric version thereof or an antigen binding fragment thereof with said tissue sample; and
   determining binding thereof with said tissue sample; whereby the presence of said cancerous cells in said tissue sample is indicated.

11. A method of treating a human tumor in a mammal, wherein said human tumor expresses at least one epitope of an antigen which is specifically bound by the isolated monoclonal antibody produced by the hybridoma deposited with the IDAC as accession number 170505-04, a humanized version thereof, a chimeric version thereof, an antigen binding fragment thereof or at least one isolated monoclonal antibody or antigen binding fragment thereof that specifically binds to the same epitope or epitopes as those recognized by the isolated monoclonal antibody produced by a hybridoma cell line AR62A61.8 having IDAC Accession No. 170505-04, comprising administering to said mammal said monoclonal antibody or antigen binding fragment thereof in an amount effective to result in a reduction of said mammal's tumor burden.

12. The method of claim 11 wherein said isolated monoclonal antibody antigen binding fragment thereof is conjugated to a cytotoxic moiety.

13. The method of claim 12 wherein said cytotoxic moiety is a radioactive isotope.

14. The method of claim 11 wherein said isolated monoclonal antibody or antigen binding fragment thereof activates complement.

15. The method of claim 11 wherein said isolated monoclonal antibody or antigen binding fragment thereof mediates cellular cytotoxicity.

16. A method of treating a human tumor susceptible to antibody induced cellular cytotoxicity in a mammal, wherein said human tumor expresses at least one epitope of an antigen which is specifically bound by the isolated monoclonal antibody produced by the hybridoma deposited with the IDAC as accession number 170505-04, a humanized version thereof, a chimeric version thereof, an antigen binding fragment thereof or at least one isolated monoclonal antibody or antigen binding fragment thereof that specifically binds to the same epitope or epitopes as those recognized by the isolated monoclonal antibody AR62A61.8 having IDAC Accession No. 170505-04, comprising administering to said mammal said monoclonal antibody or an antigen binding fragment thereof in an amount effective to result in a reduction of said mammal's tumor burden.

17. A The method of claim 16 wherein said isolated monoclonal antibody or antigen binding fragment thereof is conjugated to a cytotoxic moiety.

18. The method of claim 17 wherein said cytotoxic moiety is a radioactive isotope.

19. The method of claim 17 wherein said 16 wherein said isolated monoclonal antibody or antigen binding fragment thereof activates complement.

20. The method of claim 16 wherein said isolated monoclonal antibody or antigen binding fragment thereof mediates cellular cytotoxicity.

* * * * *